United States Patent [19]

Morris et al.

[11] Patent Number: 5,712,151
[45] Date of Patent: Jan. 27, 1998

[54] ANTIFUNGAL AGENT

[75] Inventors: Sandra A. Morris, Westfield; Gerald F. Bills, Clark; James E. Curotto, Morgan; Sarah J. Dreikorn, Scotch Plains, all of N.J.; Angela Basilio, Madrid, Spain; Maria Teresa Diez, Madrid, Spain; Fernando Pelaez, Madrid, Spain; Francisca Vicente, Madrid, Spain; Bruce W. Burgess, Passaic, N.J.; Stanley L. Streicher, Verona, N.J.; Deborah L. Zink, Manalapan, N.J.; John R. Thompson, Scotch Plains, N.J.

[73] Assignee: Merck & Co., Inc., Rahway, N.J.

[21] Appl. No.: 734,702

[22] Filed: Oct. 21, 1996

Related U.S. Application Data

[60] Provisional application No. 60/008,081 Oct. 30, 1995.
[51] Int. Cl.⁶ .................. C12N 5/00; C12N 5/02
[52] U.S. Cl. .............. 435/254.1; 435/117; 435/118; 514/408; 514/411; 548/400

[58] Field of Search ................ 435/117, 254.1, 435/118; 514/408, 411; 548/400

*Primary Examiner*—Leon B. Lankford, Jr.
*Attorney, Agent, or Firm*—Elliott Korsen; Mark R. Daniel

[57] ABSTRACT

There is disclosed a novel compound having the formula

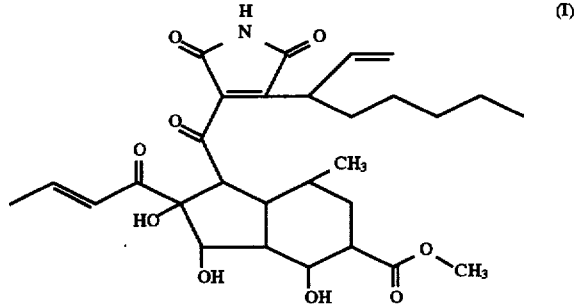

which exhibits antifungal activity.

7 Claims, No Drawings

ANTIFUNGAL AGENT

This application claims priority to U.S. Provisional Patent Application Ser. Nos. 60/008/081, filed Oct. 30, 1995 and 60/008,956, filed Dec. 20, 1995.

BACKGROUND OF THE INVENTION

The present invention relates to novel antifungal compounds, compositions and methods of use. The compound and compositions exhibit broad spectrum antifungal activity against both human and plant fungal pathogens. Clinical treatment of human fungal infections has relied mainly on two types of antifungal agents. These agents are amphotericin B, which is fungicidal and capable of curing fungal infections at the cost of severe side effects to the patient, and ketoconazole and other azole agents, which exhibit fewer side effects but are only fungistatic.

Thus, there is a need for new human antifungal agents.

SUMMARY OF THE INVENTION

The present invention is directed to the compound of the formula (I):

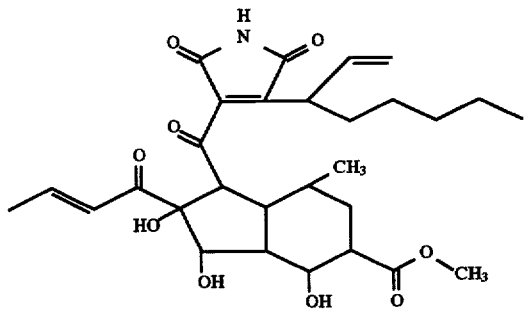

The compound has antimicrobial and fungicidal properties and may be useful for controlling systemic and superficial fungal infections in humans with fewer side effects than standard antifungal agents such as amphotericin B or ketoconazole.

The compounds are obtained by cultivation of a strain of Chaetosphaeronema, MF 6188 in the culture collection of Merck & Co., Inc., Rahway, N.J.

DETAILED DESCRIPTION OF THE INVENTION

The compound is colorless and characterized by the following spectral properties:

Ultraviolet Spectral Data $\lambda_{max}$(MeOH): 234 nm

Infrared Spectral Data

Recorded as a thin film on ZnSe: 3245, 2929, 1717, 1624, 1439, 1206, 1142, 724 cm$^{-1}$

Mass Spectral Data

Mass spectra were recorded on JEOL SX-102A (Electron Impact, EI, 90 eV), JEOL HX110 (Fast Atom Bombardment, FAB), and TSQ70B (LC/MS-ESI, Liquid Chromatography-Electrospray Ionization) mass spectrometers. The FAB spectrum was run in a matrix of dithiothreitol-dithioerythritol (20/80). The exact mass measurements were made at high resolution with Ultramark™ 1960 (Fomblin) as the reference compound.

HR FAB-MS Found: 546.2691 Calculated for $C_{29}H_{39}NO_9+H$: 546.2703

NMR Spectral Data

NMR spectra were recorded in acetone-$d_6$ at 500 MHz ($^1H$) or 125 MHz ($^{13}C$). Chemical shifts are reported downfield from TMS (tetramethylsilane) and spectra were referenced to the solvent peak (2.05 ppm for $^1H$ spectra and 29.9 ppm for $^{13}C$ spectra).

$^1H$ NMR Spectra

δ $^1H$: 9.81(br s; 1H), 6.86(dq; 15.5, 6.6; 1H), 6.74(dq; 15.5, 1.5; 1H), 6.11(ddd; 17.4, 10.0, 8.3; 1H), 5.26(ddd; 17.4, 1.5, 0.7; 1H), 5.10(dd; 10.0, 1.5; 1H), 4.79(br s; 1H), 4.66 (br s; 1H), 4.05(d; 4.8; 1H), 3.93(d; 10.7; 1H), 3.83(dt; 8.3, 7.2; 1H), 3.65(s; 3H), 2.80(ddd; 1H), 2.61(ddd; 12.6, 4.4, 2.2; 1H), 1.80(dd; 6.6, 1.5; 3H), 1.77(m; 1H), 1.73(m; 2H), 1.67(m; 2H), 1.42(m; 1H), 1.35(m; 1H), 1.28(m; 4H), 1.25(m; 1H), 0.87(t; 7.2; 3H), 0.84(d; 6.7; 3H) ppm $^{13}C$ NMR Spectra δ $^{13}C$: 201.2(s), 196.0(s), 173.7(s), 170.6(s), 170.4(s), 152.6(s), 145.0(d), 138.2(d), 135.9(s); 126.1(d), 118.6(t), 87.0(s), 77.6(d), 68.7(d), 63.0(d), 51.7(q), 49.6(d), 48.5(d), 42.9(d), 41.3(d), 37.9(d), 33.9(t), 32.1(t), 31.6(t), 27.8(t), 23.1(t), 21.7(q), 18.5(q), 14.3(q) ppm The compound of this invention has antimicrobial properties and is especially useful as an antifungal agent against both filamentous fungi and yeasts. It is useful against organisms causing systemic human pathogenic mycotic infections such as Candida albicans, Candida tropicalis, Candida guillermondii, Candida glabrata, Cryptococcus neofromans, Aspergillus fumigatus, Candida pseudotropicalis, Saccharomyces cerevisiae, Aspergillus flavus et al. It is also useful against organisms causing superficial fungal infections such as Trichoderma sp. and Candida sp. These properties may be effectively utilized by administering compositions containing an antifungal amount of the compound to an area, object or subject, on or in which fungi are to be controlled. Thus, compositions containing an antifungally effective amount of the compound and their use for the control of fungi are aspects of the present invention. An especially preferred aspect of the present invention are compositions in a pharmaceutically acceptable carrier and their use for the control of mycotic infections by administering a therapeutically effective amount of one or both of the compounds.

The compound of the present invention is a natural product produced from a strain of Chaetosphaeronema (Coelomycetes, Deuteromycotina), MF 6188 in the culture collection of Merck & Co., Inc., Rahway, N.J., which has been deposited under the Budapest Treaty in the culture collection of the American Type Culture Collection on Nov. 29, 1995 at 12301 Parklawn Drive, Rockville, Md. 20852 and assigned accession number ATCC 74354.

The producing organism is a strain of Chaetosphaeronema (Coelomycetes, Deuteromycotina) that was isolated from forest leaf litter, collected in Cuarros de Garabito, Puntarenas Province, Costa Rica.

In agar culture, colonies of the fungus exhibit the following morphology:

Colonies on oatmeal agar (Difco) at 25° C., 12 hr photoperiod attaining 35–37 mm in 14 days, with advancing zone submerged, even, with aerial mycelium scant to velvety or woolly, dull, obscurely zonate, with some radial sectors, at first white to pale gray to dark olive gray, Dawn Gray, Storm Gray, Castor Gray (capitalized color names from Ridgway, R. 1912. Color Standards and Nomenclature. Published by the author. Washington, D.C.), with reverse dull grayish brown, exudates absent.

Colonies on potato-dextrose agar (Difco) at 25° C., 12 hr photoperiod attaining 40–42 mm in 14 days, submerged to appressed at the margin, raised towards the center, velvety to woolly, obscurely zonate, dull, white to pale gray, finally dark olivaceous gray, Olive-Gray, Storm Gray, Castor Gray, Dusky Green-Gray, reverse pale ochraceous gray to dark brownish gray Clay Color, Tawny-Olive, Saccardo's Umber, exudates absent.

Colonies on YM agar (Difco) at 25° C., 12 hr photoperiod attaining 39–40 mm in 14 days, with margin submerged, even, raised, velvety, with some radial sectors, azonate, pale brownish gray to gray, finally dark brownish gray, similar to color on oatmeal agar, reverse dark brownish gray, exudates absent. Some slight growth at 37° C., about 1–2 mm in 14 days.

Mycelium composed of highly branched, simple septate, thin- to slightly thick-walled, dematiaceous hyphae characteristic of many ascomycetous fungi. In older cultures intercalary dictyochlamydospores form on the aerial hyphae, especially towards the outer edges of the Petri plates. Dictyochlamydospores elongated along the main axis of the hyphae, consisting of irregular masses of slightly thick-walled, dark cells, with individual cells up to 12 μm in diameter.

Conidiomata formed abundantly on autoclaved banana leave supported by cornmeal agar (Difco) or scattered around the edges of mature cultures (>3 weeks old) on YM agar. Conidiomata are pycnida, dark olivaceous brown, discrete, scattered, partially imbedded in leaf tissue, subglobose, 200–400 μm in diameter, centrally papillate with a single ostiole, hairy, with hairs slightly thick-walled, septate, dark olivaceous brown, up to 200 μm long. Conidiomatal wall composed of dark, tightly woven hyphae, easily rupturing, with inner wall lined with conidiogenous cells.

Conidiogenous cells enteroblastic, phialidic, hyaline, cylindrical or tapered toward apex, with or without a slightly flared collerette, branched once or twice at the base, with periclinal thickenings at conidiogenous locus, 8–12×2.5–3.5 μm.

Conidia cylindrical, to allantoid, occasionally eccentrically curved, broadly rounded or sometimes inflated at the apices or bases, 1-septate, smooth, hyaline, without appendages, 9.5–12×3–4 μm, exuding from mature conidiomata in a whitish to translucent mass.

Pycnidial fungi, such as the producing organism, without an apparent sexual reproductive phase, are referred to the form class Coelomycetes. Following the diagnostic system of Sutton (Sutton, B. C. 1980. The Coelomycetes. Commonwealth Mycological Institute, Kew, United Kingdom), the discrete, thin-walled pycnidia with phialidic conidiogenous cells would place this organism among Sutton's Blastopycnidiae. Within this group of genera, the producing organism would best fit the concept of Chaetosphaeronema (Sutton pg. 408) based on the combination of hairy-setose, ostiolate pycnidia, elongated and sparsely branched phialides, and elongated, 1-septate conidia.

Although the invention is discussed principally with respect to the specific strain, it is well known in the art that the properties of microorganisms can be varied naturally and artificially. Thus, all strains of the sterile fungus MF 6188, ATCC 74354 including varieties and mutants, whether obtained by natural selection, produced by the action of mutating agents such as ionizing radiation or ultraviolet irradiation, or by the action of chemical mutagens such as nitrosoguanidine, are contemplated to be within the scope of this invention.

The production of the compound may be carried out by cultivating the sterile fungus MF 6188, ATCC 74354 in a suitable nutrient medium under conditions described herein until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate the compound from other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium. These, however, are merely illustrative of the wide variety of media which may be employed and are not intended to be limiting.

TABLE 1

| KF SEED MEDIUM | | Trace Element Mix | |
|---|---|---|---|
| | per liter | | per liter |
| Corn Steep Liquor | 5 g | $FeSO_4.7H_2O$ | 1 g |
| Tomato Paste | 40 g | $MnSO_4.4H_2O$ | 1 g |
| Oat flour | 10 g | $CUCl_2.2H_2O$ | 25 mg |
| Glucose | 10 g | $CaCl_2$ | 100 mg |
| Trace Element Mix | 10 ml | $H_3BO_3$ | 56 mg |
| | | $(NH_4)_6Mo_7O_{24}.4H_2O$ | 19 mg |
| | | $ZnSO_4.7H_2O$ | 200 mg | pH = 6.8

TABLE 2

| PRODUCTION MEDIUM CYS80 | |
|---|---|
| Component | per liter |
| Sucrose | 80 g |
| Corn Meal (yellow) | 50 g |
| Yeast Extract | 1 g |

No pH adjustment

TABLE 3

PRODUCTION MEDIUM STP

| Component | per liter |
| --- | --- |
| Sucrose | 75 g |
| Tomato Paste | 10 g |
| Malt Extract | 5 g |
| $(NH_4)_2SO_4$ | 1 g |
| Soy Flour | 1 g |
| $KH_2PO_4$ | 9 g | pH adjusted to 7.0 with NaOH before autoclaving

Of the foregoing media, the STP medium, was found to give the best yield of the compound. In the production of the compound, generally, the culture is first grown in a seed medium and the culture growth then used to inoculate a production medium. The production medium may be a solid medium or a liquid medium.

The culture was maintained in sterile soil and stored at 4° C. until ready for use. The seed culture was inoculated by aseptically transferring a small amount of the preserved soil into a 250 ml Erlenmeyer flask containing 50 mls of seed medium of the following composition (in g/liter); corn steep liquor, 5.0; tomato paste, 40.0; oat flour, 10.0; glucose, 10.0; and trace elements solution, 10 mls/liter (consisting of, in g/liter: $FeSO_4.7H_2O$, 1.0; $MnSO_4.4H_2O$, 1.0; $CuCl_2.2H_2O$, 0.025; $CaCl_2.2H_2O$, 0.1; $H_3BO_3$, 0.056; $(NH_4)_6MoO_{24}.4H_2O$, 0.019; $ZnSO_4.7H_2O$, 0.2; dissolved in 0.6N HCl). Seed medium was prepared with distilled water, the pH was adjusted to 6.8 by adding NaOH and the medium dispensed into 250 ml Erlenmeyer flasks and capped with cotton plugs before being autoclaved at 121° C. for 20 minutes. The seed culture was incubated at 25° C. on a gyrotory shaker (220 rpm, 5.1 cm throw) for 66 hours prior to the inoculation of fermentation flasks.

The STP production medium was prepared using distilled water; 50 mls medium was dispensed into 250 ml Erlenmeyer flasks that were capped with cotton plugs before being autoclaved at 121° C. for 20 minutes. Production flasks were inoculated with 2.0 mls vegetative seed growth and were incubated at 25° C., on a gyrotory shaker (220 rpm, 5.1 cm throw) for 14 to 17 days. After the incubation period, each production flask was homogenized, extracted with 50.0 mls of methanol, shaken for 30 minutes, pooled and delivered for the isolation of active compounds.

The usefulness of the compound as an antifungal agent, especially as an antimycotic agent, may be demonstrated with the compound in a broth microdilution assay for the determination of minimum inhibitory concentration (MIC) and minimum fungicidal concentration (MFC) against fungi. In such assay against a panel of fungi selected for their resistance/susceptibility to known compounds, animal virulence, source and clinical importance, the compound is found to be effective at concentrations comparable to an established antifungal agent, amphotericin B.

In the microbroth dilution assay, microorganisms were selected by streaking a yeast culture on Sabouraud dextrose agar (SDA) incubating for 24–48 hours at 35°–37° C., thereafter selected 3 to 5 characteristic colonies and transferring to a fresh plate and incubating under similar conditions. From the regrowth, 3 to 5 colonies were selected and suspended in 10 milliliters of YM broth (Difco) and incubated for 4 hours at 35°–37° C. shaking at 225 rpm. The 4 hour broth cultures were adjusted optically to 86% transmission resulting in a concentration of $1-5\times10^6$ cfu/ml which was further diluted 1:100 in YNBD (yeast nitrogen base with 1% dextrose) to obtain a concentration of $1-5\times10^4$ cfu/ml for use as inocula.

The test compound was dissolved at 256 µg/ml in 10% DMSO and diluted 2× into the first well to achieve a concentration of 256 µg/ml at 5% DMSO in the first well. Compounds are subsequently serially diluted 2× and cell suspension is added to each well resulting in an additional 2× dilution of compound. 75 µl of said solution is delivered to each well in column 1 of a 96-well, U-bottomed microtiter plate. The compounds in column 1 were then serially diluted two-fold to yield concentrations from 64 µg/ml to 0.03 µg/ml.

Amphotericin B, the control compound, was prepared as a stock solution of 512 µg/ml in 10% DMSO and 75 µl of said solution delivered to column 1 of a 96-well, U-bottomed microtiter plate. The compounds in column 1 were then serially diluted two-fold to yield concentrations from 128 µg/ml to 0.06 µg/ml.

The plates containing the diluted compounds were then inoculated with 75 µl/well of the appropriate microorganism and incubated for 48 hours at 35°–37° C. with MIC (minimum inhibitory concentration) determinations carried out after 24 hours of incubation (except Cryptococcus strains which are read at 48 hours). Growth and sterility controls for each organism and sterility checks for the compounds also were carried out.

After recording MICs at 24 hours, the microtiter plates were shaken gently to resuspend the cells. A 1.5 µl sample was transferred from each well of the 96-well microtiter plate to a single reservoir inoculum plate containing SDA. The inoculated SDA and corresponding microtiter plates were incubated for 24 hours at 35°–37° C. For *Cryptococcus neoformans*, SDA plates were inoculated at 48 hours after recording MICs and incubated 48 hours before reading the MFC. MFC is the lowest concentration of compound at which either no growth or growth of ≦4 colonies occur.

| Minimum Fungicidal Concentration (MFC) Minimum Inhibitory Concentration (MIC) µg/ml | | |
| --- | --- | --- |
| Strain | MIC | MFC |
| *Candida albicans* (MY1055) | <0.03 | 0.06 |
| *Candida glabrata* (MY1381) | 16 | 32 |
| *Candida parapsilosis* (MY1010) | <0.03 | <0.03 |
| *Candida pseudotropicalis* (MY2099) | 2 | 4 |
| *Candida tropicalis* (MY1124) | 4 | 8 |
| *Candida albicans* (CLY539) | 0.06 | 0.125 |
| *Candida albicans* (CA2) | 0.125 | 0.25 |
| *Candida tropicalis* (MY1012) | 1 | 2 |
| *Candida guillermondii* (MY1019) | 2 | 16 |
| *Candida krusei* | 0.06 | 0.5 |
| *Cryptococcus neoformans* (MY2061) | <0.03 | <0.93 |
| *Cryptococcus neoformans* (MY2062) | <0.03 | <0.03 |
| *Saccharomyces cerevisiae* (MY2140) | 4 | 0.5 |
| *Aspergillus fumigatus* (MY4839) | <0.03 | |
| *Aspergillus fumigatus* (MY5668) | 1 | |

The compound is also useful for inhibiting the growth of filamentous fungi. Such use may be illustrated in the following tests with *Aspergillus flavus, Fusarium oxysporum, Ustilago zeae* and the like.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

The samples to be tested for production of antifungal agent are applied directly to the agar plates as methanol solutions. When the sample to be tested is crude broth, it may be centrifuged prior to application. The assay plates are then incubated at either 28° C. or 37° C. for 24 hours. Following incubation, the inhibition zones are measured.

Growths are also noted as to appearance. The compound is seen to effectively inhibit growth of the fungal organisms.

In view of the broad spectrum of activity, the product of the present invention either singly or as a mixture is adaptable to being utilized in various applications of antifungal compositions. In such case, compounds may be admixed with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compound may be admixed with a pharmaceutically acceptable carrier, the nature of which will depend on whether the composition is to be topical, parenteral or oral.

If said application is to be topical, the drug may be formulated in conventional creams and ointments such as white petrolatum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by mixing the component drugs with any of the usual pharmaceutical media, including for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricants such as calcium stearate, together with binders, disintegrating agents and the like.

These compositions are then administered in amounts sufficient to obtain the desired antifungal effect. For medical applications, the method comprises administering to a subject in need of treatment a therapeutically effective antifungal amount of the compounds. The appropriate dose will vary depending on age, severity, body weight and other conditions. For topical application, the compositions are applied directly to the area where control is desired. For internal administration, the composition may be applied by injection or may be administered orally.

For non-medical application, the product of the present invention, either alone or as a mixture, may be employed in compositions in an inert carrier which included finely divided dry or liquid diluents, extenders, fillers, conditioners and excipients, including various clays, diatomaceous earth, talc, and the like or water and various organic liquids such as lower alkanols, such as ethanol and isopropanol, or kerosene, benzene, toluene and other petroleum distillate fractions or mixtures thereof.

The following example illustrates the invention but is not to be construed as limiting the invention disclosed herein.

EXAMPLE I

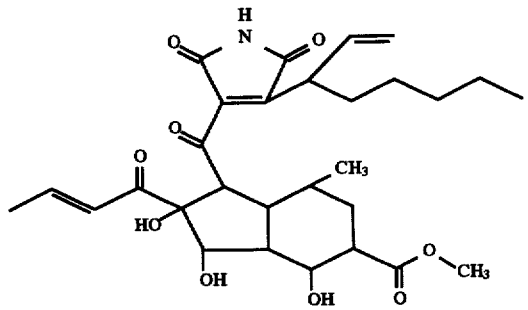

Isolation

The isolation procedure involved: 1) partitioning of the MEK extract between EtOAc and H₂O, 2) separation of the EtOAc extracted material by open reversed phase C-8 chromatography (60% ACN/40% H₂O), 3) HPLC purification on Zorbax RX-C8 (75% MeOH/25% H₂O) and 4) a final HPLC purification on Zorbax RX-C8 (60% ACN/40% [0.1% aq. TFA]). This procedure resulted in a >95% pure (based on nmr and HPLC) preparation of the compound. The overall recovery of material was 19% using this procedure (400× purification).

Compound I had the spectral properties previously described.

The following examples illustrate representative compositions containing Compound I.

EXAMPLE A 1000 compressed tablets each containing 500 milligrams of Compound I are prepared from the following formulation:

|  | Grams |
| --- | --- |
| Compound I | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 milligrams of Compound I are prepared from the following formulation:

| Compound I | 500 |
| --- | --- |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 milliliters of an injectible solution are prepared by conventional procedures from the following formulation:

| Dextrose | 12.5 grams |
| --- | --- |
| Water | 250 milliliters |
| Compound I | 406 milligrams |

The ingredients are blended and thereafter sterilized for use.

EXAMPLE D

An ointment suitable for topical application may be prepared by intimately dispersing 13 mg of Compound I in 1 g of commercially available polyethylene/hydrocarbon gel.

EXAMPLE E

An aerosol composition may be prepared having the following formulation (per canister):

| | |
|---|---|
| Compound I | 24 mg |
| Lecithin NF, liquid concentrate | 1.2 mg |
| Trichlorofluoromethane | 4.025 g |
| Dichlorodefluoromethane | 12.15 g |

What is claimed is:

1. A substantially pure compound having the structure:

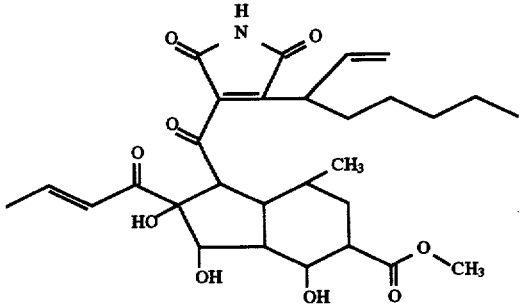

(I)

2. An antifungal composition comprising an antifungal amount of the compound of claim 1 in admixture with a biologically inert carrier or diluent.

3. A composition according to claim 2 wherein the carrier is a pharmaceutically acceptable carrier.

4. A method for controlling fungal growth which comprises administering to the site where growth is to be controlled, an effective amount of the compound of claim 1.

5. A method for combatting fungal infections in mammals which comprises administering to a region of the animal afflicted with said fungi a therapeutically effective amount of the compound of claim 1.

6. A process for producing the compound of claim 1 which comprises aerobically cultivating a culture of ATCC 74354 in a nutrient medium containing assimilable sources of carbon and nitrogen and isolating said compound therefrom.

7. A biologically pure culture of fungus (ATCC 74354) capable of producing the compound of claim 1 in recoverable amounts.

* * * * *